United States Patent
Dondzillo et al.

(10) Patent No.: US 9,458,420 B2
(45) Date of Patent: Oct. 4, 2016

(54) SYSTEM AND METHODS FOR CONDUCTING IN VITRO EXPERIMENTS

(71) Applicant: The Regents of the University of Colorado, A Body Corporate, Denver, CO (US)

(72) Inventors: Anna Dondzillo, Denver, CO (US); Achim Klug, Denver, CO (US); Tim C. Lei, Thornton, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 0 days.

(21) Appl. No.: 14/483,883

(22) Filed: Sep. 11, 2014

(65) Prior Publication Data
US 2015/0072372 A1    Mar. 12, 2015

Related U.S. Application Data

(60) Provisional application No. 61/876,664, filed on Sep. 11, 2013.

(51) Int. Cl.
*C12M 1/34*  (2006.01)
*C12M 3/00*  (2006.01)
*C12M 1/12*  (2006.01)
*C12M 1/00*  (2006.01)

(52) U.S. Cl.
CPC ............ *C12M 21/08* (2013.01); *C12M 23/04* (2013.01); *C12M 23/34* (2013.01); *C12M 27/20* (2013.01); *C12M 41/34* (2013.01)

(58) Field of Classification Search
CPC .... C12M 21/08; C12M 23/04; C12M 23/34; C12M 27/20; C12M 41/34
See application file for complete search history.

(56) References Cited

U.S. PATENT DOCUMENTS

2011/0256574 A1\* 10/2011 Zhang ............... B01L 3/502761
                                                                  435/29

\* cited by examiner

*Primary Examiner* — Michael Hobbs
(74) *Attorney, Agent, or Firm* — Valauskas Corder LLC (57) ABSTRACT

A system and methods by which in vitro experiments directed to a subject may be managed more efficiently including the more efficient use of a nutrient solution used in certain in vitro experimentation. Certain embodiments of the system and methods may include a retainer in which the subject of the experimentation and a nutrient solution is retainable and a recycling component that facilitates the restoration or reconditioning of the nutrient solution during the period of experimentation.

7 Claims, 10 Drawing Sheets

SYSTEM AND METHODS FOR CONDUCTING IN VITRO EXPERIMENTS

CROSS REFERENCE TO RELATED APPLICATIONS

This application claims the benefit of U.S. provisional application 61/876,664 filed Sep. 11, 2013, which is incorporated by reference herein in its entirety.

GOVERNMENT INTEREST STATEMENT

This invention was made with government support under R01 DC 011583 awarded by National Institutes of Health (NIH). The government has certain rights in the invention.

FIELD OF THE INVENTION

The present invention is a system and methods by which in vitro experiments directed to a subject may be managed more efficiently. More particularly, the present invention is a system and methods that facilitate the more efficient use of the nutrients and the nutrient solution used in certain in vitro experimentation.

BACKGROUND OF THE INVENTION

Scientists conduct investigations or experiments that are often categorized as "in vivo" or "in vitro". For purposes of this application, the term "in vivo" means "in the living" and "in vivo experiments" are experiments conducted using complete living organisms. An example of an in vivo experiment includes administering a drug to a human or a live mouse and observing or testing whether the drug has the intended effect and/or any side effects.

The term "in vitro" means "in the glass", for example, in a test tube or in a petri dish. As such, in vitro experiments are experiments conducted not within a non-living organism but instead on only part of an organism, such as cells or biological molecules, or outside the organism's normal biological context.

For purposes of this application, the term "subject" will be used to refer that to which an experiment is directed such as cells, groups of cells, tissues, organs, entire organisms, or any other biological subject of experimentation.

An advantage of in vivo experiments is that the subject of the experimentation is still operating within the subject's normal biological context (e.g., in a population or ecosystem). Accordingly, any experimental manipulations performed in vivo are considered to be most representative of the situation under observation or review. However, often such experiments are not practical or not considered ethical. Therefore, in vitro experiments are sometimes used as a substitute.

For example, when a scientist wishes to study a subject in vitro, he or she may remove representative cells, groups of cells, or portion from an organism, then observe the isolated subject, and possibly introduce some experimental variable. Introducing an experimental variable may include changing something in the surroundings (e.g., temperature, pressure, light conditions, concentration of certain chemicals in an aquatic environment), or involve the administration of a substance to which a subject is not typically exposed. After introducing the variable, the scientist may observe or otherwise assess, detect, or measure whether any change has occurred in the subject. If there is a change in the subject, it may be caused by or at least be correlated with the introduction of the experimental variable.

In certain experiments, scientists may attempt to control the factors that are not being studied as the variable in order to minimize or eliminate any effect on the subject caused by those factors. This is generally easier to do in vitro with an isolated subject than in an entire living organism. Scientists may attempt also to simulate the conditions for a subject in vivo, and, accordingly, facilitate observing any effect or correlation resulting from treatment with the variable.

Certain devices have been developed to facilitate controlling the in vitro environment and simulating in vivo conditions. For example, when a subject is a cell or a tissue, a scientist may wish to observe or treat the subject while it is alive. A cell or tissue subject may need certain chemicals, gases, nutrients, or other requirements to stay alive and possibly grow. Examples of such requirements are glucose or pyruvate, for cellular energy sources, myo-inositol for intracellular calcium control and maintenance of membrane potentials, oxygen to sustain the aerobic metabolism, or growth factors. Accordingly, the device in such circumstances may be in a dish in which the subject cell or cell tissue is positioned in a solution containing at least the chemicals, gases, and/or nutrients that are needed by the subject to be kept in the condition required for the experiment. This solution containing at least the required or critical components will be termed "nutrient solution" for purposes of this application. Anyone of such required components may be generically identified in this application as a "nutrient".

As time passes, the cell/tissue that is the subject of the experiment may consume one or more of a critical component, such as oxygen or glucose, from the nutrient solution. Accordingly, the concentration of the critical component in the solution may decrease. For example, many experimental subjects require oxygen or carbon dioxide to maintain cellular processes. Because the concentration of this gaseous nutrient will decrease over time in the nutrient solution, certain known devices are configured to permit the nutrient solution to be "bubbled" with oxygen or carbon dioxide, However, many such known devices do not facilitate the atmospheric conditions associated with the nutrient solution to be monitored and managed. As a result, the balance of such a critical component relative to the solution may be altered over time and, for example, the cellular processes to be affected or the pH of the solution to become imbalanced.

Alternatively, certain known devices attempt to manage the issue of a loss of one or more critical component in the device over time by permitting the original nutrient solution to be released from the dish after a certain period of time, and discarded. Additional nutrient solution may then be permitted to flow into the dish from a storage container. Some other known devices achieve this same goal by establishing a continuous inflow of solution from an external reservoir and matching outflow. In such other known devices, fresh nutrient solution enters the device from one side while spent nutrient solution exits the device from the opposite side, establishing a continuous unidirectional flow of nutrient solution across the subject of the experiment. While these types of devices and replenishment systems may keep the subject cell or tissue exposed to the necessary components in the appropriate concentration, the components of the nutrient solution not consumed by the cell or tissue are discarded generally as waste. Discarding all the nutrient solution, including those components that were not consumed, altered, or made ineffective during the course of the experiment is especially problematic when one or more of the components of the solution are rare, expensive, or otherwise difficult to mix or maintain.

Whenever nutrient solution is valuable, the amount that is used and possibly wasted must be reduced. Certain techniques and devices have been developed in order to achieve this objective, some of which are the following. One technique reduces the rate at which solution enters and leaves the device, thereby reducing the overall consumption of nutrient solution. Another technique and device does not discard the spent solution exiting the device but instead collects and recycles it.

However, many known devices and techniques that seek to improve the efficiencies of in vitro experimentation have one or more disadvantages associated with them. For example, the techniques and devices that seek to collect and recycle spent solution largely all require a variety of additional components with which the complete volume of solution that was in the experimental area can exit the area and be held and processed—including to add in any nutrient that may have been depleted during the experiment—and the processed solution added back into the experimental area. The need for such additional components—such as tubing, containers, and pumps—all add to the cost of the experiment. Also, in order to establish the needed fluid circulation from the experimental area through these additional collection and recycling components and back to the experimental area, a volume of nutrient solution much larger than the amount needed in the immediate experimental area is required. Even the most volume-conservative existing devices require a total fluid volume of at least 8-10 ml in order to establish fluid circulation. If the nutrient solution or at least a component of the nutrient solution is rare, expensive, or otherwise difficult to obtain, 8-10 mL may be an amount that is larger than that which can be readily prepared.

Clearly, there is a demand for a more efficient and cost effective system and methods to manage the nutrient solutions used in experimentation. The present invention satisfies this demand.

SUMMARY OF INVENTION

The present invention is a system and methods by which the in vitro experiments directed to a subject may be managed more efficiently. More particularly, the present invention is a system and methods that facilitate the more efficient use of the nutrient solution used in certain in vitro experimentation.

Certain embodiments of a retainer, according to the present invention, are configured to retain the subject of the experiment and a nutrient solution. Examples of a subject of an experiment, including a cell or tissue sample, is generally identified in this application as "subject". A nutrient solution generally has a composition that maintains the subject in the state needed to conduct the experiment.

Certain embodiments of the present invention provide what is termed for purposes of this application as a "self-contained" system and related methods that include or utilize a retainer in which the subject of the experiment is positionable and that is configurable to permit the reuse of one or more of the components of the nutrient solution directly within the retainer and without the need for the entire volume of nutrient solution to be withdrawn from the retainer. Such a self-contained system and methods may be configured advantageously to reduce disruptions to the subject during the course of the experiment since the nutrient solution may not need to be withdrawn from the retainer. Also, certain embodiments of the self-contained system and methods are configurable to eliminate the need for the conventional additional storage container, pump, or tube components that form a portion of for known systems that recycle the complete volume of nutrient solution used for in vitro experimentation. Because the certain self-contained embodiments of the present invention do not require largely more nutrient solution that is necessary to conduct the experiment, the overall cost of each experiment is lower than those conducted with conventional systems and methods. That an amount of an expensive nutrient may be unexpectedly confined to or lost in the tubing or other components needed in conventional systems that recycle the nutrient solution is eliminated.

In order to permit certain embodiments of the present invention to operate as a self-contained system as that term is defined for purposes of this application—that is, one in which the nutrient solution needed for an experiment is largely reused without leaving it the retainer—, embodiments of the present invention may include components that restore one or more of the nutrients that may be depleted during the course of the experiment, all without the need to remove the larger portion of the nutrient solution within the retainer. An example of a nutrient that may be added to the nutrient solution within the retainer is oxygen. A retainer may be sized and shaped to operate with an restoration component configured to increase the nutrient depleted or lost during the experiment, such as the oxygen level in the solution, such as through the use of external tubing. By permitting the nutrient solution to be reused in place in the retainer, and any nutrient that was depleted during the experimentation to be restored to the solution—for example, if a gas was depleted during the experiment by enriching it with gas directly in the retainer—, the total amount of nutrient solution required to maintain the subject of the experiment is reduced significantly below the 8-10 mL amount conventionally required in certain known devices. Advantageously, certain embodiments of the present invention can reduce the total volume required for an experiment to about 1.6 to 2.5 ml total.

Additional embodiments of the present invention may include a retainer that includes a removal element that facilitates the removal or release of some component that has developed in the nutrient solution during the course of the experiment, such as another gas, carbon dioxide.

Certain embodiments of the present invention also may include a controller component configured to permit manage and control at least one nutrient level in the solution.

One objective of certain embodiments of the present invention is to provide a system and methods for which the amount of nutrients and the volume of nutrient solution needed to keep the subject of an experiment alive is minimized.

Another objective of certain embodiments of the present invention is to provide a system and methods for which the need for additional recycling containers, tubes, or external pumps to manage a nutrient solution during the course of an experiment is largely eliminated.

An additional objective of certain embodiments of the present invention is to optimize the circulation of nutrient solution during the course of an experiment.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to the limit the invention, where like designations denote like elements, and in which.

DETAILED DESCRIPTION OF EMBODIMENTS OF THE INVENTION

Figure 1A:
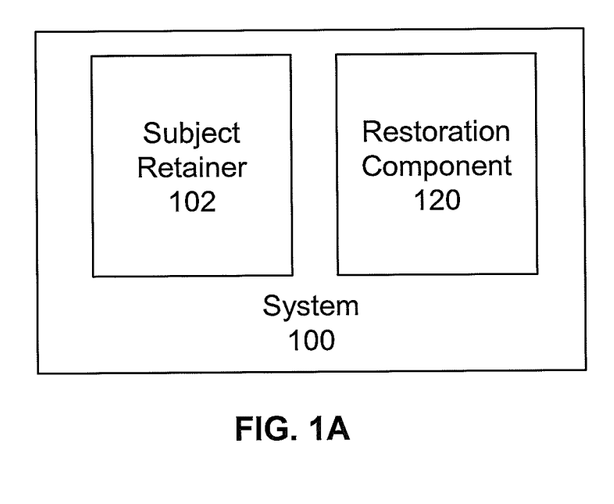
FIG. 1A illustrates an embodiment of a system according to the present invention.
Figure 1B:
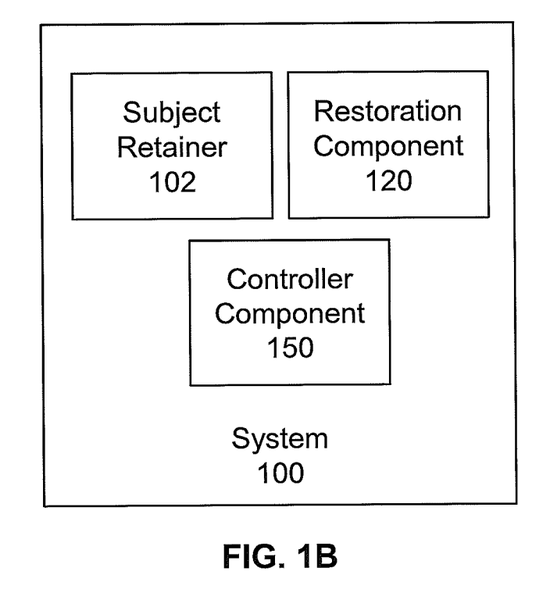
FIG. 1B illustrates another embodiment of a system according to the present invention.

Certain embodiments of the present invention include a system 100 having a subject retainer 102 (also termed "retainer" for purposes of this application) and a restoration component 120 as illustrated in FIG. 1A. Embodiments of the present invention may include a system having also a controller component 150, as illustrated in FIG. 1B.

A retainer 102 may be configured to retain at least the subject of the experiment and the volume of a nutrient solution needed to conduct the experiment on the subject. Certain embodiments of the retainer 102 may be sized and shaped such that the retainer is similarly sized and shaped to a standard glass slide. Advantageously, such a sized and shaped retainer allows the subject of the experiment to be easily viewed under a microscope that is configured to receive a standard glass slide.

The retainer 102 may include a retainer wall 103 certain embodiments of which may include at least side wall 104 and a bottom wall 108 that made from a material or materials and are configured to form a retainer space 103A in which a nutrient solution (not shown) may be retained and the experimentation subject 101 positioned. In the self-contained embodiments of the present invention, the retainer space 103A that is formed by at least side wall 104 and bottom wall 108 is sized and shaped to receive and retain the volume of nutrient solution that is appropriate for the subject, nature, and length of the experiment. An experiment conducted on a certain subject may be of such a short length that the retainer space 103A may be sized to hold a smaller amount of nutrient solution while another experiment on another subject may take longer and therefore may require a larger retainer space 103A that can accommodate a larger volume of nutrient solution.

Figure 2A:
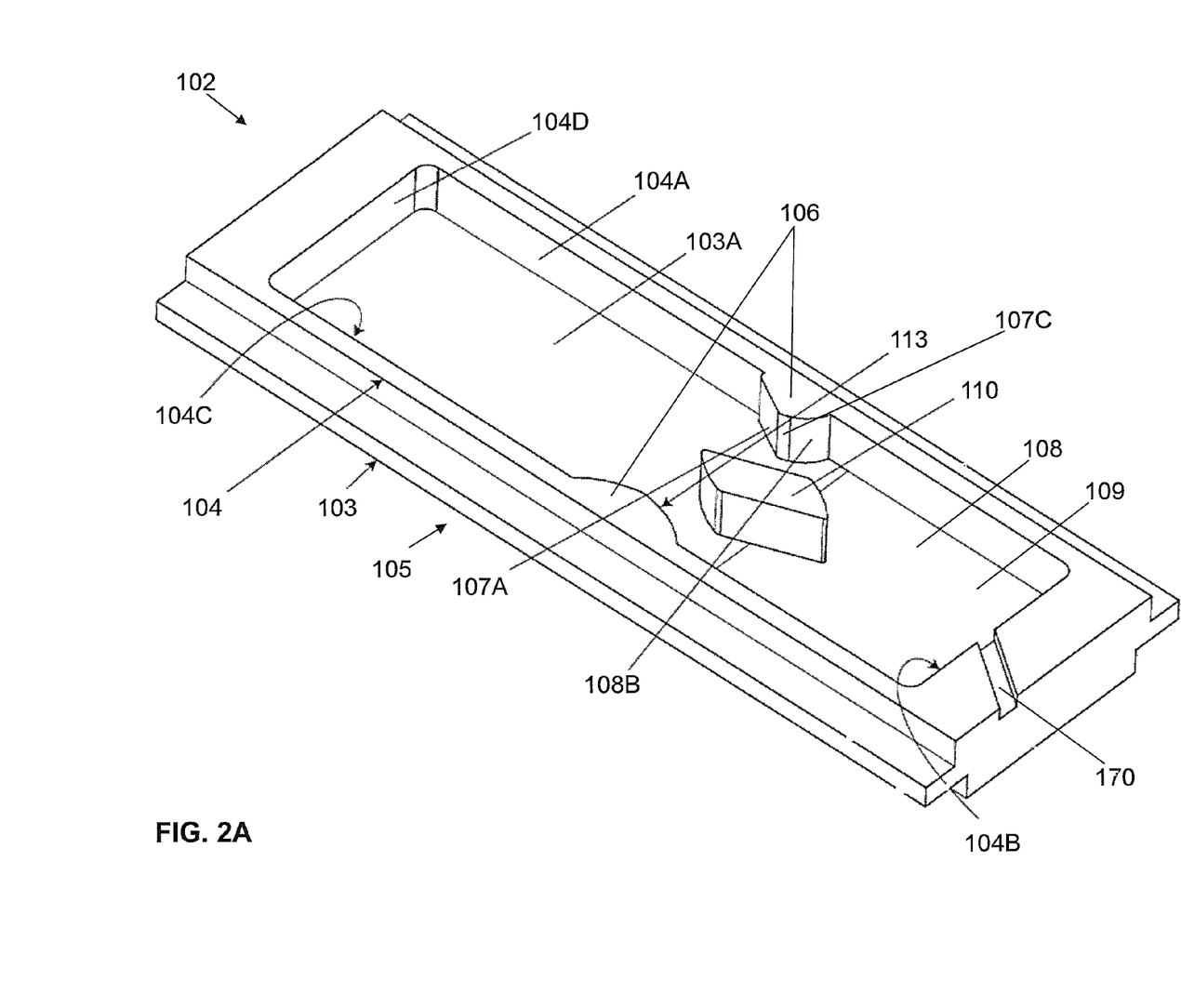
FIG. 2A illustrates a perspective view of an embodiment of a subject retainer according to the present invention.
Figure 4:
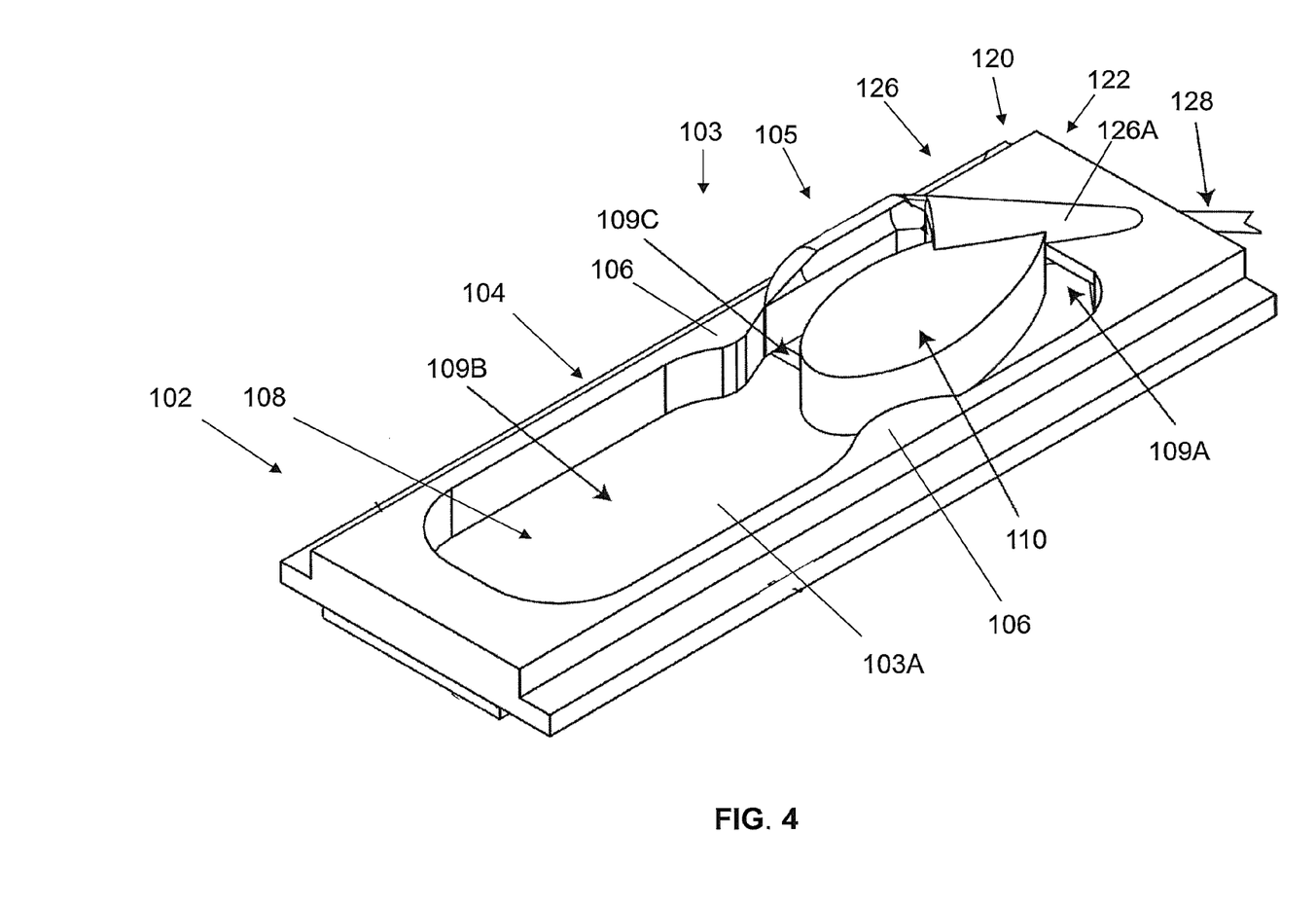
FIG. 4 illustrates a perspective view of an embodiment of a subject retainer that includes an oxygenation component according to the present invention.

The side wall 104 may include a first retainer side wall 104A, second retainer side wall 104B, third retainer side wall 104C, and a fourth retainer side wall 104D. The retainer 102 also may include a retainer bottom wall 108. In certain embodiments, the retainer bottom wall 108 may be configured to provide a uniplanar upper surface 109, as illustrated in FIG. 2A. In other embodiments, the retainer bottom wall 108 may include other surface configurations including those having not a uniplanar bottom upper surface, for example, ones in which at least a portion of the bottom upper surface is generally vertical, generally curved, or generally slanted. To illustrate, the embodiment shown in FIG. 4 includes a first bottom upper surface 109A and a second bottom upper surface 109B, each of which are generally horizontal bottom surfaces. In certain such embodiments, such as the embodiment shown in FIG. 4, the first bottom upper surface 109A is positioned in a different plane than the second bottom upper surface 109B with a third bottom upper surface 109C configured as a generally vertical surface that connects the two generally horizontal surfaces, 109A and 109B.

Figure 5:
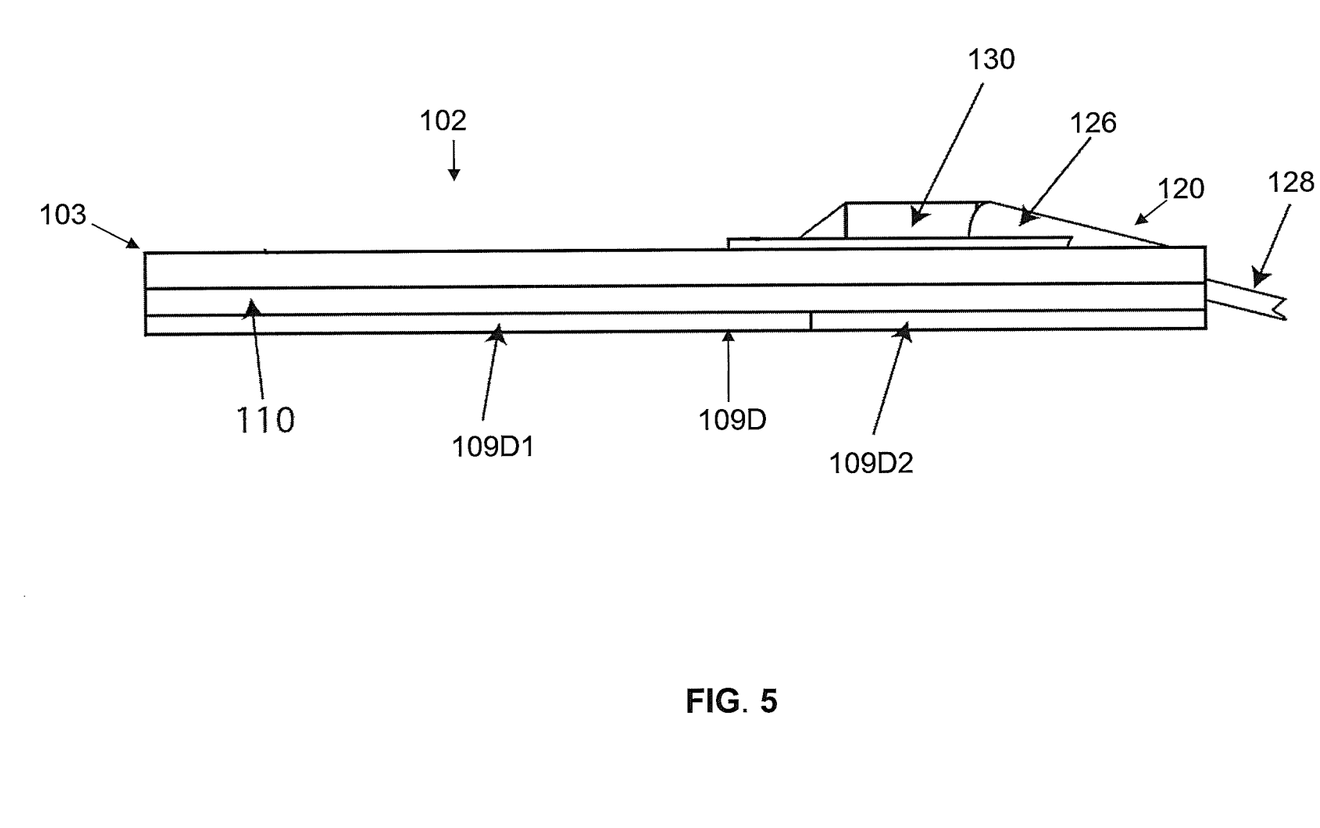
FIG. 5 illustrates a side profile view of an embodiment of a subject retainer according to the present invention.

The retainer bottom wall 108 may be made from one or more materials and configured to be generally transparent to permit the illumination of the subject from below or viewing a background below or behind the retainer bottom wall 108. To facilitate such illumination or viewing, the retainer may include a lower support element 109D that may include a clear component 109D1 and a bottom plate 109D2 such as shown in FIG. 5. In another embodiment, the lower support element 109D can form a generally continuous component.

Certain embodiments of the present invention include a restoration component 120 configured to restore at least one nutrient in the nutrient solution. In certain experiments, and with certain embodiments of the present invention, oxygen may be the nutrient of those in the nutrient solution that is most likely to be depleted during the course of the experiment. Oxygen may be depleted more quickly than other nutrients because it may be consumed not only by the subject, but also may be lost to the atmosphere during the course of the experiment. Accordingly, certain embodiments of the present invention may include a restoration component 120 that includes an oxygenation component 122 that facilitates adding oxygen to the nutrient solution. An oxygenation component 122 may include a gas cylinder 124 (shown in FIG. 2B and FIG. 2C) and a delivery component 126. Certain embodiments of the delivery component 126 include an oxygen distribution element 128 and a solution exchange element 130, to which a cover 126A may be added.

Figure 2B:
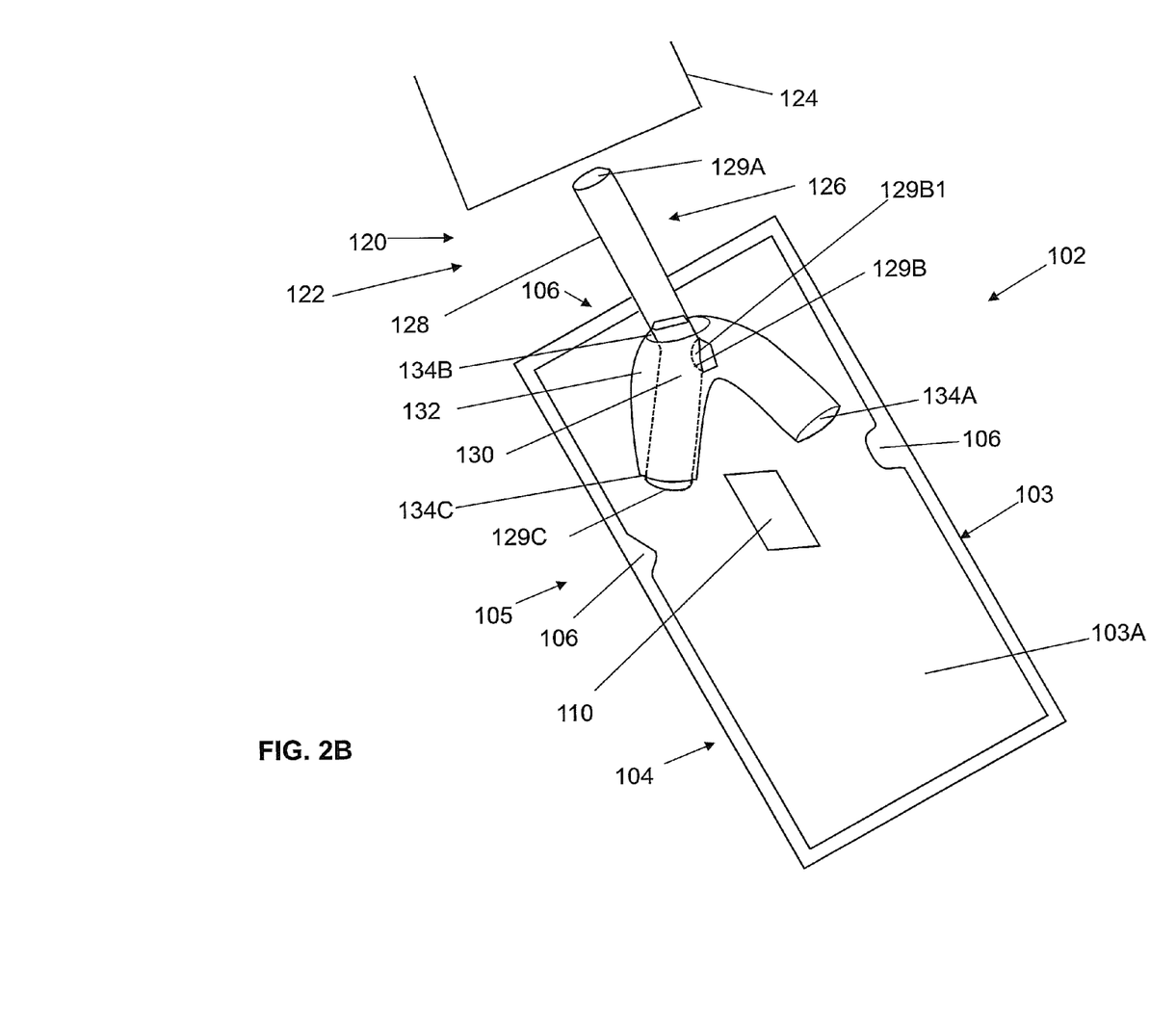
FIG. 2B illustrates a perspective view of an embodiment of a subject retainer and a reuse component according to the present invention.

As shown in FIG. 2B, certain embodiments of the present invention may include an oxygen distribution element 128 that is tubular in construction and having an oxygen input end 129A, a solution input element 129B, and a combination output end 129C. The oxygen input end 129B may be configured to receive oxygen (or another nutrient) from the gas cylinder 124. The solution input element 129B may include a rim defining an aperture 129B1 through which nutrient solution may enter the oxygen distribution element 128. Advantageously, the oxygen may mix with the nutrient solution generally inside the oxygen distribution element 128 nearby the solution input element 129B in an area called the solution exchange element 130. With such mixing, oxygen-enriched nutrient solution may then be released through the output end 129C into the retainer space 103A. A fine-mesh, a grid or other similar devices can be inserted or installed to the recycling output or other parts of the recycling system to reduce gas bubbles or other disturbance to improve the oxygen-enrichment or the solution circulation and recirculation process.

As shown in FIG. 2B, the delivery component 126 also may include a liquid transfer component 132. The liquid transfer component 132 may include a liquid input element 134A, oxygen delivery receiving opening 134B, and a solution exchange holder 134C.

Each end of the tubular oxygen distribution element 128 shown in FIG. 2A may be designed to permit the mix of oxygen (air) and nutrient solution liquid flow out of the combination output end 129C while simultaneously sucking the liquid up into the oxygen delivery component 128 from the other liquid transfer component 132. The result may be a jet that facilitates the propulsion of the nutrient solution into a circulatory motion around the retainer space 103A.

Figure 2C:
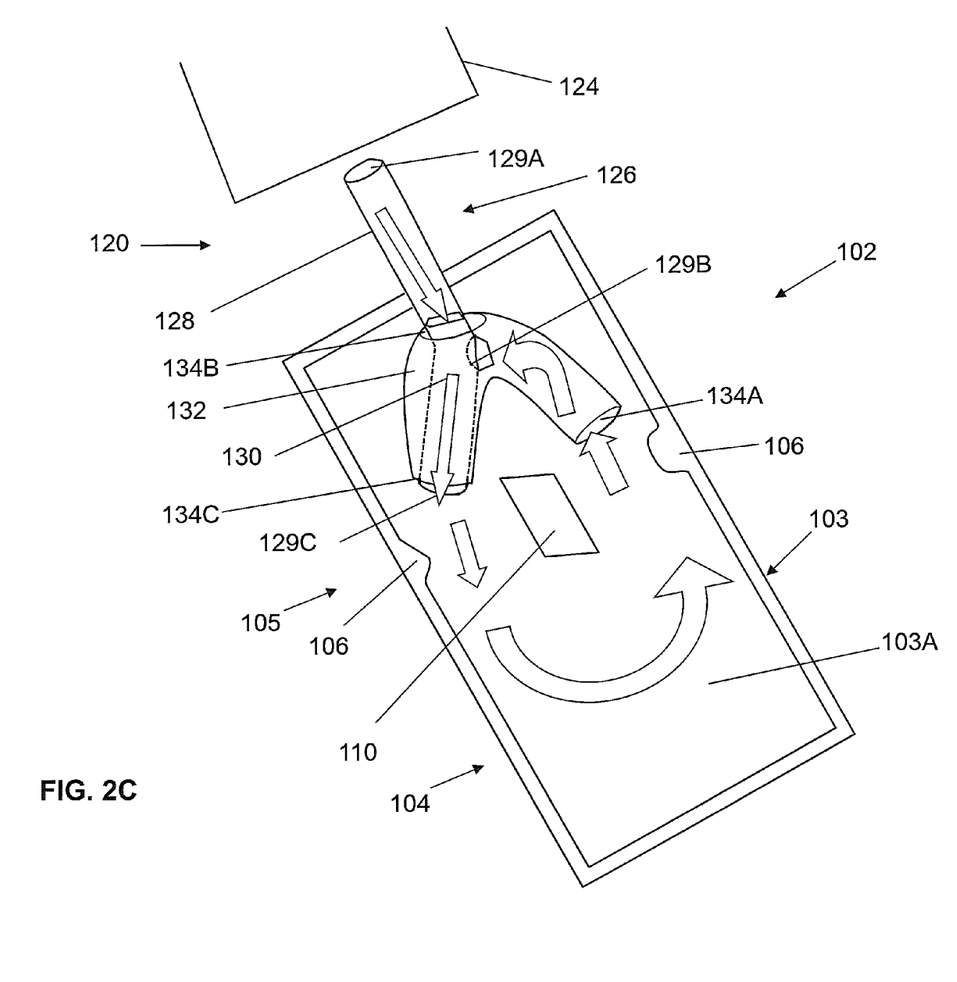
FIG. 2C illustrates a perspective view of an embodiment of a subject retainer and a reuse component according to the present invention.

Certain embodiments of the present invention may include one or more circulation components 105 that facilitate the circulation of a solution within a retainer used, for example, for experimentation. Certain embodiments of the circulation components 105 include one or more protrusion elements 106 including protrusion surfaces 107 and a guiding component 110. As illustrated in FIG. 2A, two of the opposing side walls, e.g., the first retainer side wall 104A and third retainer side wall 104C, may include a protrusion wall element 106. The size and shape of the protrusion wall elements 106 may be configured to not only facilitate the circulation of the nutrient solution but also to define the volume of the retainer 103A and therefore the amount of nutrient solution needed to fill the retainer space 103A. Each protrusion wall element 106 includes a protrusion surface 107 that, depending on the circulation effect that is sought, may have a single configuration or a plurality of configurations. The embodiment illustrated in FIG. 2A, includes a protrusion wall element 106 having a protrusion surface 107 with a first protrusion surface 107A, a second protrusion surface 107B, and a third protrusion surface 107C. In the FIG. 2A embodiment, the first protrusion surface 107A is vertical and generally not curved, the second protrusion surface 107B is vertical and generally curved, and the third protrusion surface 107C is in a vertical plane that is different but connects with the planes in which the first protrusion surface 107A and second protrusion surface 107B are positioned. The retainer may include one or more additional protrusion wall elements 106. The embodiment illustrated in FIG. 2A includes a second protrusion wall element 106—that extends the surface of the surface 104C of the side wall 104 into the retainer space 103A—having a fourth protrusion surface 113. In the embodiment illustrated in FIG. 2A, the fourth protrusion surface 113 is configured as a generally curved vertical surface. Such features of the walls that define the retainer space facilitate the effective circulation of nutrient solution, and a circulation pattern that is stable for a wide range of fluid circulation speeds. The arrows in FIG. 2C illustrate an example of such circulatory motion that may be developed within the retainer space 103A.

To further facilitate the solution circulation within the retainer 103, certain embodiments of the present invention may include a guiding component 110. Certain embodiments of the guiding component 110 may be positioned to extend from the retainer bottom wall 108 and to facilitate the generally circular motion of the nutrient solution around the retainer space 103. The guiding component 110 may be of any shape to facilitate such circulation—including any polygon or wave-type shape—and to define the amount of nutrient solution that is required to fill the retainer space 103A.

In certain embodiments of the present invention, a second retainer side wall 104B includes a groove component 170 configured to receive some portion or component of the restoration component 120.

In addition to a restoration component 120, certain embodiments of the present invention may include a mini-motor to enhance the propulsion of the liquid between the liquid input element 134A and the combination output end 129C.

The subject retainer 102 also may be configured to include a byproducts component configured to extract or release byproducts generated by the subject of the experiment from the solution. However, in embodiments that form a closed system, and accordingly, do not include a byproducts component, the ratio of byproduct built up to solution is one of the limiting factors for minimizing the amount of nutrient solution to maintain a functioning system.

In addition to a subject retainer 102, certain embodiments of the present invention may include a controller component 150 as part of the system 100. A controller component 150 is configured to permit controlling one or more nutrient levels in a nutrient solution. For example, the controller component 150 may permit a user to turn on or turn off the oxygenation component, or regulate the temperature, bath level of the nutrient solution, or speed of a mini-motor. Examples of a controller component 150 include a computer system or a cloud computing system.

Figure 3A:
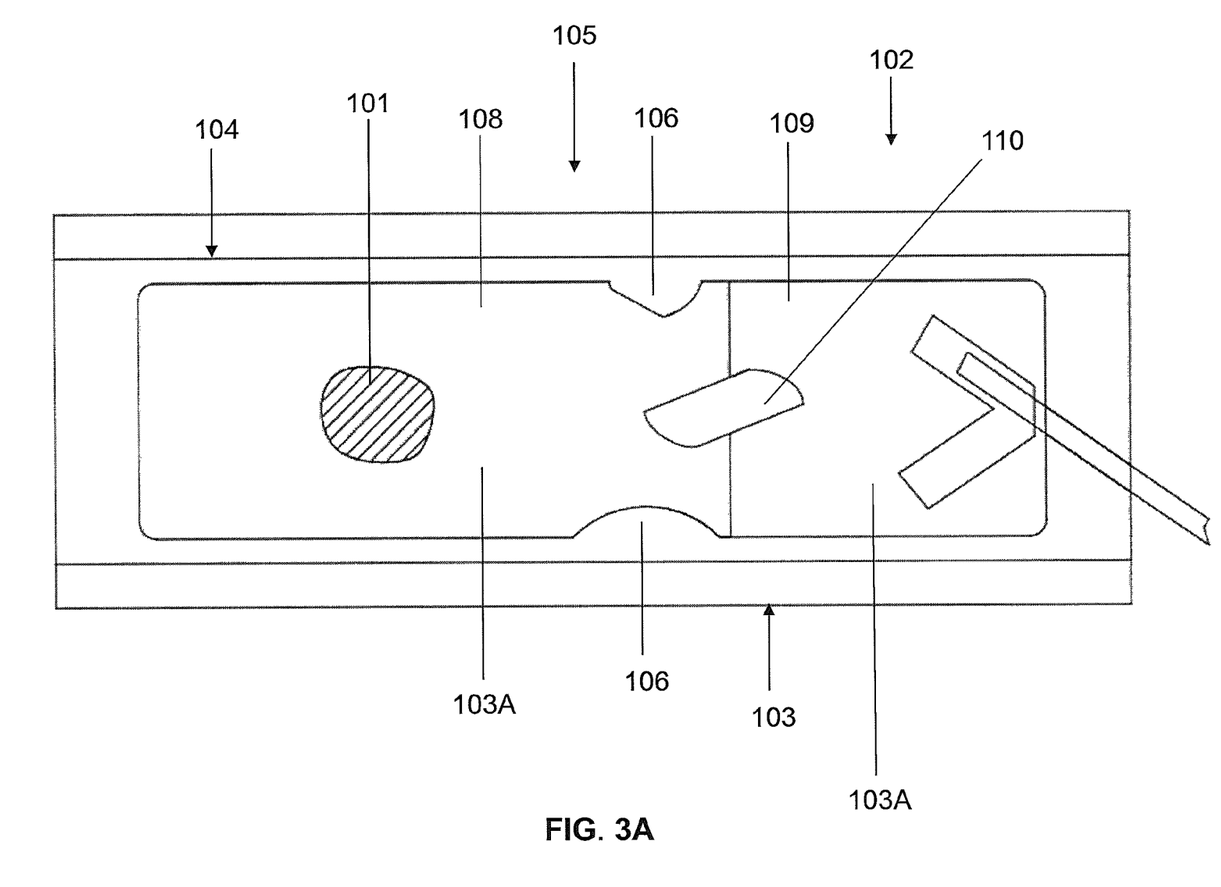
FIG. 3A illustrates a top view of an embodiment of the present invention in which the subject retainer includes the subject of the experiment.
Figure 3B:
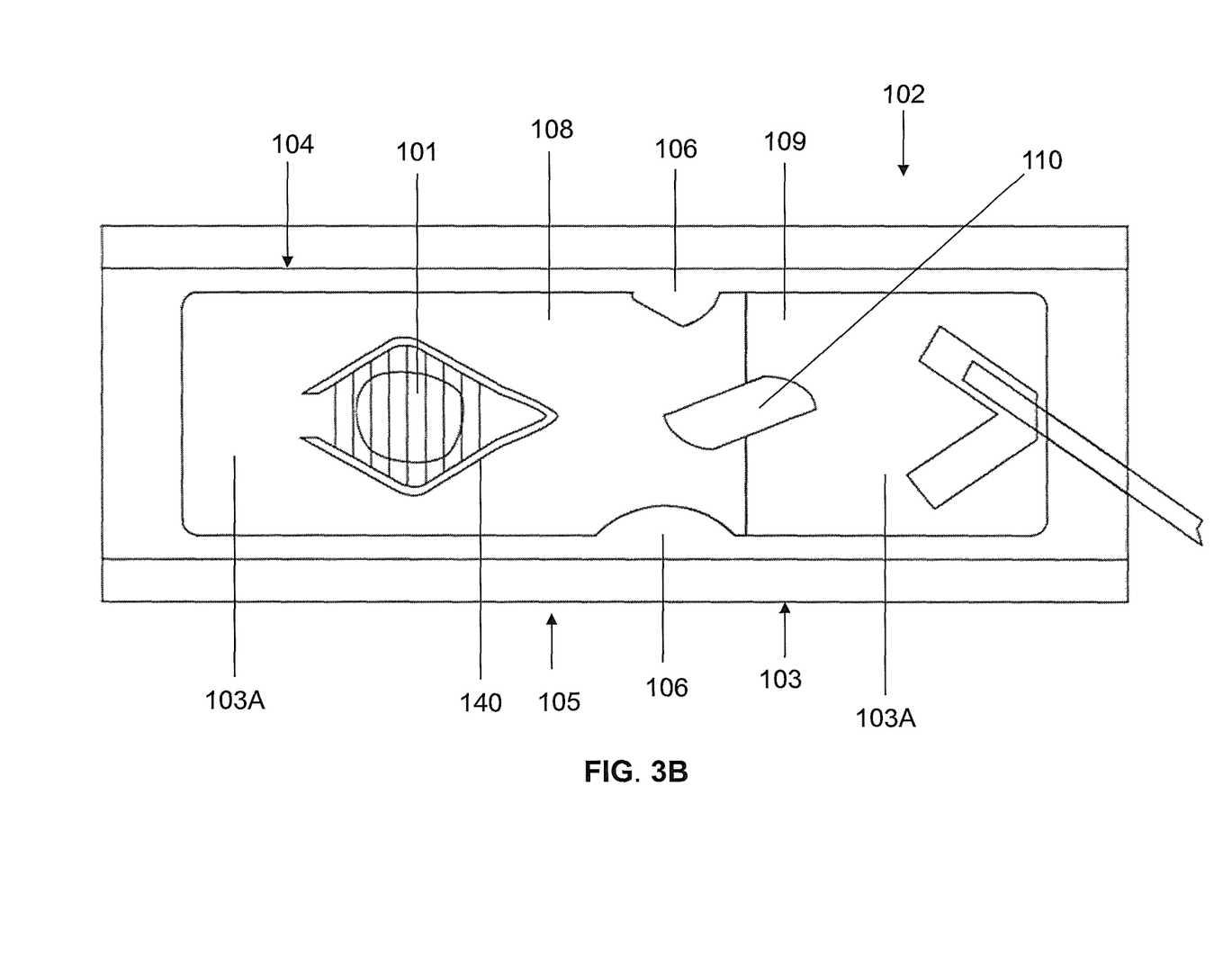
FIG. 3B illustrates a top view of an embodiment of the present invention in which the subject retainer includes the subject of the experiment positioned by a hold down component.

FIG. 3A illustrates an embodiment of the present invention in which a subject 101 is positioned in a portion of the retainer space 103A. FIG. 3B illustrates an embodiment of the subject retainer having a hold down component 140 configured to maintain the subject in a particular location within the retainer space 103A.

Certain embodiments of a subject retainer may be manufactured using a three-dimensional printer, casting, injection molding, machining, or other process appropriate for the specific embodiment being manufactured.

Certain embodiments of a subject retainer may contain sensors or transducers, such as oxygen sensors, PH sensors, glucose sensors, water level sensors, and other sensors, to allow monitoring the conditions of the device.

Figure 6:
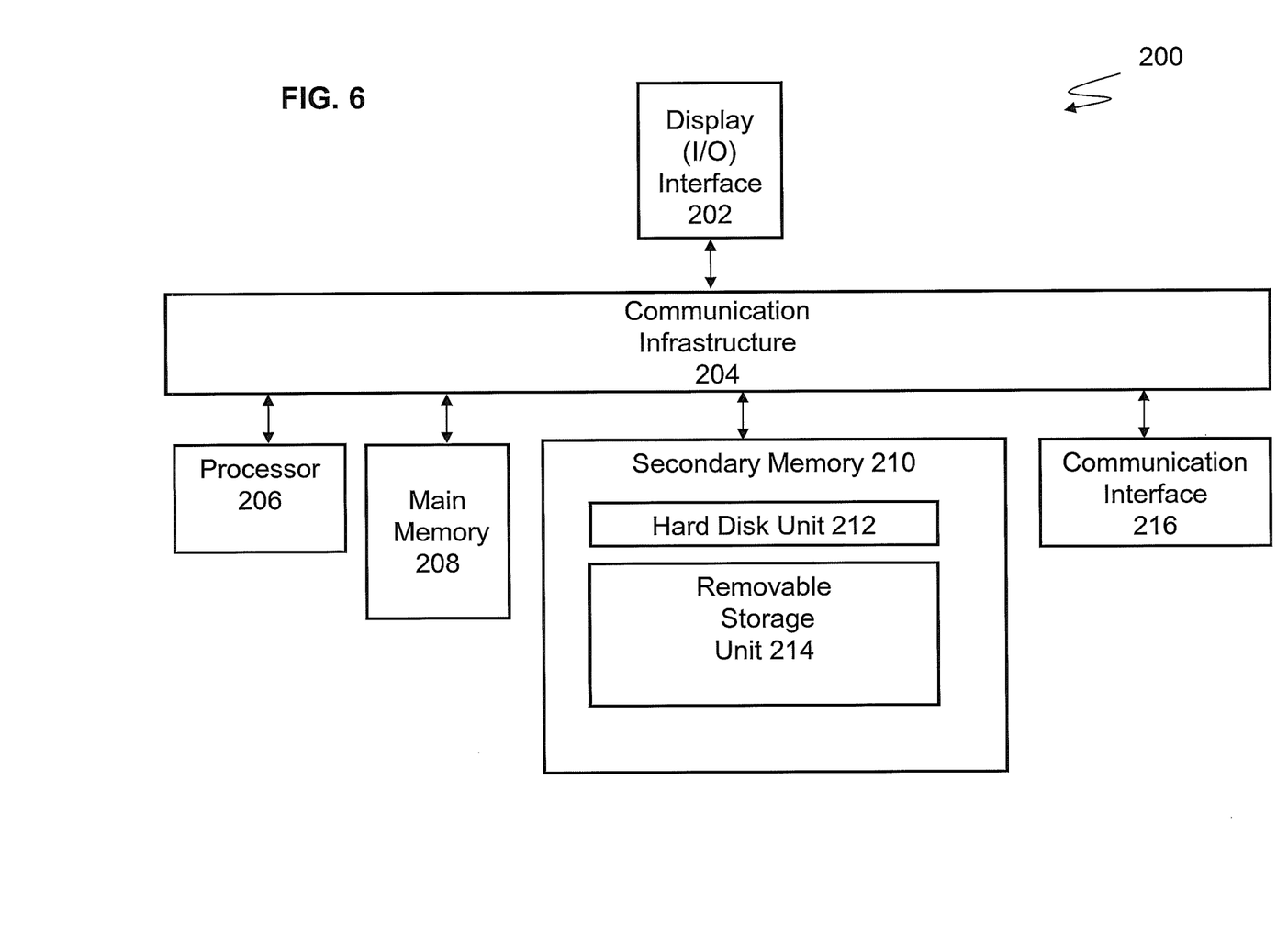
FIG. 6 illustrates an exemplary computer system according to the present invention.

FIG. 6 illustrates an exemplary computer system 200 that may be used to implement the methods according to the invention. One or more computer systems 200 may carry out the methods presented herein as computer code.

Computer system 200 includes an input/output display interface 202 connected to communication infrastructure 204—such as a bus—, which forwards data such as graphics, text, and information, from the communication infrastructure 204 or from a frame buffer (not shown) to other components of the computer system 200. The input/output display interface 202 may be, for example, a keyboard, touch screen, joystick, trackball, mouse, monitor, speaker, printer, any other computer peripheral device, or any combination thereof, capable of entering and/or viewing data.

Computer system 200 includes one or more processors 206, which may be a special purpose or a general-purpose digital signal processor that processes certain information. Computer system 200 also includes a main memory 208, for example random access memory ("RAM"), read-only memory ("ROM"), mass storage device, or any combination thereof. Computer system 200 may also include a secondary memory 210 such as a hard disk unit 212, a removable storage unit 214, or any combination thereof. Computer system 200 may also include a communication interface 216, for example, a modem, a network interface (such as an Ethernet card or Ethernet cable), a communication port, a PCMCIA slot and card, wired or wireless systems (such as Wi-Fi, Bluetooth, Infrared), local area networks, wide area networks, intranets, etc.

It is contemplated that the main memory 208, secondary memory 210, communication interface 216, or a combination thereof, function as a computer usable storage medium, otherwise referred to as a computer readable storage medium, to store and/or access computer software including computer instructions. For example, computer programs or other instructions may be loaded into the computer system 200 such as through a removable storage device, for example, a floppy disk, ZIP disks, magnetic tape, portable flash drive, optical disk such as a CD or DVD or Blu-ray, Micro-Electro-Mechanical Systems ("MEMS"), nano-technological apparatus. Specifically, computer software including computer instructions may be transferred from the removable storage unit 214 or hard disc unit 212 to the secondary memory 210 or through the communication infrastructure 204 to the main memory 208 of the computer system 200.

The computer system can also be designed using other embedded, miniaturized, or single-chip computer techniques, such as using "System on a Chip" system (i.e. Raspberry Pi), "Field Programming Gate Array (FPGA)" system, programmable soft CPU core, stand-alone "Digital Signal Processors (DSP)", or other similar techniques to implement computer algorithm to control the system or the recycling process. The computer algorithm can simply be turning the oxygen gas on and off based on the reading of the sensors placed inside or outside of the device. Or other sophisticated computer algorithms such as Proportional-Integral-Derivative (PID), Fourier Transform, Lapace Transform, Principal Component Analysis (PCA) or other control algorithms or implementations to control the device or recycling process.

Communication interface 216 allows software, instructions and data to be transferred between the computer system 200 and external devices or external networks. Software, instructions, and/or data transferred by the communication interface 216 are typically in the form of signals that may be electronic, electromagnetic, optical, or other signals capable of being sent and received by the communication interface 216. Signals may be sent and received using wire or cable, fiber optics, a phone line, a cellular phone link, a Radio Frequency ("RF") link, wireless link, or other communication channels.

Computer programs, when executed, enable the computer system 200, particularly the processor 206, to implement the methods of the invention according to computer software including instructions.

The computer system 200 described herein may perform any one of, or any combination of, the steps of any of the methods presented herein. It is also contemplated that the methods according to the invention may be performed automatically, or may be invoked by some form of manual intervention.

The computer system 200 of FIG. 6 is provided only for purposes of illustration, such that the invention is not limited to this specific embodiment. It is appreciated that a person skilled in the relevant art knows how to program and implement the invention using any computer system.

The computer system 200 may be a handheld device and include any small-sized computer device including, for example, a personal digital assistant ("PDA"), smart handheld computing device, cellular telephone, or a laptop or netbook computer, hand held console or MP3 player, tablet, or similar hand held computer device, such as an iPad®, iPad Touch® or iPhone®.

Figure 7:
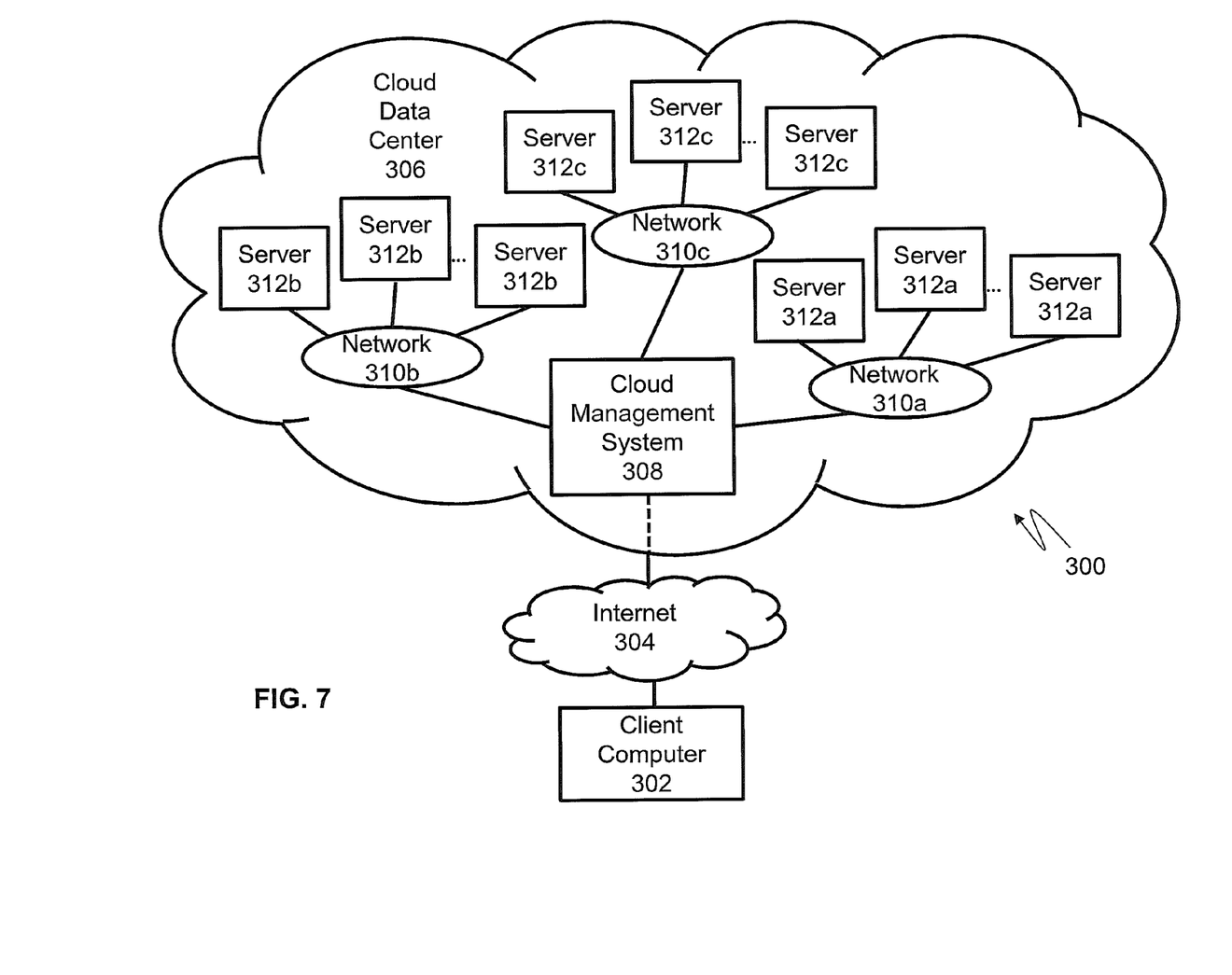
FIG. 7 illustrates a cloud computing system according to the present invention.

FIG. 7 illustrates an exemplary cloud computing system 300 that may be used to implement the methods according to the present invention. The cloud computing system 300 includes a plurality of interconnected computing environments. The cloud computing system 300 utilizes the resources from various networks as a collective virtual computer, where the services and applications can run independently from a particular computer or server configuration making hardware less important.

Specifically, the cloud computing system 300 includes at least one client computer 302. The client computer 302 may be any device through the use of which a distributed computing environment may be accessed to perform the methods disclosed herein, for example, a traditional computer, portable computer, mobile phone, personal digital assistant, tablet to name a few. The client computer 302 includes memory such as random access memory ("RAM"), read-only memory ("ROM"), mass storage device, or any combination thereof. The memory functions as a computer usable storage medium, otherwise referred to as a computer readable storage medium, to store and/or access computer software and/or instructions.

The client computer 302 also includes a communications interface, for example, a modem, a network interface (such as an Ethernet card), a communications port, a PCMCIA slot and card, wired or wireless systems, etc. The communications interface allows communication through transferred signals between the client computer 302 and external devices including networks such as the Internet 304 and cloud data center 306. Communication may be implemented using wireless or wired capability such as cable, fiber optics, a phone line, a cellular phone link, radio waves or other communication channels.

The client computer 302 establishes communication with the Internet 304—specifically to one or more servers—to, in turn, establish communication with one or more cloud data centers 306. A cloud data center 306 includes one or more networks 310a, 310b, 310c managed through a cloud management system 308. Each network 310a, 310b, 310c includes resource servers 312a, 312b, 312c, respectively. Servers 312a, 312b, 312c permit access to a collection of computing resources and components that can be invoked to instantiate a virtual machine, process, or other resource for a limited or defined duration. For example, one group of resource servers can host and serve an operating system or components thereof to deliver and instantiate a virtual machine. Another group of resource servers can accept requests to host computing cycles or processor time, to supply a defined level of processing power for a virtual machine. A further group of resource servers can host and serve applications to load on an instantiation of a virtual machine, such as an email client, a browser application, a messaging application, or other applications or software.

The cloud management system 308 can comprise a dedicated or centralized server and/or other software, hardware, and network tools to communicate with one or more networks 310a, 310b, 310c, such as the Internet or other public or private network, with all sets of resource servers 312a, 312b, 312c. The cloud management system 308 may be configured to query and identify the computing resources and components managed by the set of resource servers 312a, 312b, 312c needed and available for use in the cloud data center 306. Specifically, the cloud management system 308 may be configured to identify the hardware resources and components such as type and amount of processing power, type and amount of memory, type and amount of storage, type and amount of network bandwidth and the like, of the set of resource servers 312a, 312b, 312c needed and available for use in the cloud data center 306. Likewise, the cloud management system 308 can be configured to identify the software resources and components, such as type of Operating System ("OS"), application programs, and the like, of the set of resource servers 312a, 312b, 312c needed and available for use in the cloud data center 306.

Examples of how such a computerized interface could be used are as follows:

For certain experiments that run for prolonged periods of time (overnight to several days), a sensor may measure the concentration of certain nutrients in the solution, for example oxygen. Information regarding the oxygen concentration may be fed into a computer system which may then, depending on the existing oxygen levels, increase or decrease the oxygen flow. The computer system may also record and document the nutrient concentrations as a function over time to provide assurance that the concentrations were, in fact, kept constant. Data can also be stored in cloud networks and accessed by the researcher offsite via computers or mobile devices. Remote access also allows the investigator to dial in adjustments as needed.

The present invention is also directed to computer products, otherwise referred to as computer program products, to provide software to the cloud computing system 300. Computer products store software on any computer useable medium, known now or in the future. Such software, when executed, may implement the methods according to certain embodiments of the invention. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems ("MEMS"), nano-technological storage device, etc.), and communication mediums (e.g., wired and wireless communications networks, local area networks, wide area networks, intranets, etc.). It is to be appreciated that the embodiments described herein may be implemented using software, hardware, firmware, or combinations thereof.

The cloud computing system 300 of FIG. 7 is provided only for purposes of illustration and does not limit the invention to this specific embodiment. It is appreciated that a person skilled in the relevant art knows how to program and implement the invention using any computer system or network architecture.

While the disclosure is susceptible to various modifications and alternative forms, specific exemplary embodiments of the present invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A system for reducing waste of nutrient solution used to maintain a subject during experimentation by restoring at least one nutrient of the nutrient solution depleted during the experimentation, comprising:

a retainer including a retainer wall defining a retainer space configured to accept and retain the nutrient solution and the subject during the experimentation; and a restoration component comprising an exchange element including a first input element extending to an output element, the exchange element further comprising a second input element located between the first input element and the output element, wherein the second input element and the output element are positioned within the retainer space, a first nutrient received through the first input element and the nutrient solution received through the second input element are mixed together within the exchange element and released through the output element without removal of the nutrient solution from the retainer.

2. The system according to claim 1, wherein the restoration component comprises an oxygenation component configurable to increase oxygen content of the nutrient solution.

3. The system according to claim 1, further comprising a controller element configured to permit a user to manage amounts of one or more nutrients in the nutrient solution.

4. The system according to claim 1, wherein the retainer wall includes at least a bottom wall and a side wall, the side wall including one or more protrusion elements that facilitate circulation of the nutrient solution within the retainer.

5. The system according to claim 1, further comprising a controller component configurable to control the amount of one or more nutrients within the nutrient solution.

6. The system according to claim 1, further comprising a byproducts component configurable to extract byproducts from the nutrient solution generated during the experimentation.

7. The system according to claim 1, wherein the retainer wall includes at least a bottom wall and a side wall, the bottom wall including one or more guiding components that facilitate circulation of the nutrient solution within the retainer.

* * * * *